US008685908B2

(12) United States Patent
Smith, III et al.

(10) Patent No.: US 8,685,908 B2
(45) Date of Patent: Apr. 1, 2014

(54) BAR SOAP COMPRISING PYRITHIONE SOURCES

(75) Inventors: Edward Dewey Smith, III, Mason, OH (US); Juan Wang, Beijing (CN); Xiaoyong Wang, Beijing (CN); Chunpeng Jiang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/407,252

(22) Filed: Feb. 28, 2012

(65) Prior Publication Data

US 2012/0220516 A1   Aug. 30, 2012

(30) Foreign Application Priority Data

Feb. 28, 2011 (WO) ................ PCT/CN2011/000320

(51) Int. Cl.
*A61K 8/18* (2006.01)
(52) U.S. Cl.
USPC ............................ 510/141; 510/147; 510/152
(58) Field of Classification Search
None
See application file for complete search history.

(56) References Cited

U.S. PATENT DOCUMENTS

| | | | |
|---|---|---|---|
| 2,809,971 A | 10/1957 | Bernstein et al. |
| 3,235,455 A | 2/1966 | Judge et al. |
| 3,236,733 A | 2/1966 | Karsten et al. |
| 3,281,366 A | 10/1966 | Judge et al. |
| 3,412,033 A | 11/1968 | Karsten |
| 3,725,547 A | 4/1973 | Kooistra |
| 3,753,196 A | 8/1973 | Kurtz et al. |
| 3,761,418 A | 9/1973 | Parran, Jr. |
| 3,819,431 A | 6/1974 | Kurtz et al. |
| 4,161,526 A | 7/1979 | Gorman |
| 4,323,683 A | 4/1982 | Bolich, Jr. et al. |
| 4,345,080 A | 8/1982 | Bolich, Jr. |
| 4,379,753 A | 4/1983 | Bolich, Jr. |
| 4,470,982 A | 9/1984 | Winkler |
| 4,482,715 A | 11/1984 | Trotz et al. |
| 4,533,736 A | 8/1985 | Trotz et al. |
| 4,714,563 A | 12/1987 | Kajs et al. |
| 4,818,436 A | 4/1989 | French et al. |
| 4,957,658 A | 9/1990 | French et al. |

(Continued)

FOREIGN PATENT DOCUMENTS

EP   0034385 A2   8/1981
EP   0093541 A2   11/1984

(Continued)

OTHER PUBLICATIONS

PCT International Search Report and Written Opinion dated Jul. 19, 2013.

*Primary Examiner* — Necholus Ogden, Jr.

(57) ABSTRACT

A bar soap comprising a pyrithione source, a soap surfactant, and a pH adjusting agent selected from a group consisting of ammonia solution, triethanolamine, diethanolamine, monoethanolamine, potassium hydroxide, sodium hydroxide, soluble carbonate salts, and combinations thereof, wherein the bar soap attains a pH of greater than or equal to 10.7. A process of inhibiting the formation of a discoloration in a bar soap comprising pyrithione sources by adding pH adjusting agent to attain a pH of greater than or equal to 10.7. A process of inhibiting the formation of a discoloration in a bar soap caused by dissolved ferric ions and/or cupric ions and pyrithione sources in the bar, comprising the step of adding from about 0.3% to about 20% soluble carbonate salt during manufacturing of the bar soap.

9 Claims, 1 Drawing Sheet

(56) References Cited

U.S. PATENT DOCUMENTS

| | | |
|---|---|---|
| 5,037,818 A | 8/1991 | Sime |
| 5,104,645 A | 4/1992 | Cardin et al. |
| 5,360,788 A | 11/1994 | Nelson |
| 5,403,506 A | 4/1995 | Jones |
| 5,540,860 A | 7/1996 | Hosseini et al. |
| 5,540,920 A | 7/1996 | Vinopal et al. |
| 5,573,699 A | 11/1996 | Jones et al. |
| 5,612,301 A | 3/1997 | Inman |
| 5,614,538 A | 3/1997 | Nelson, Jr. |
| 5,650,095 A | 7/1997 | Hosseini et al. |
| 5,696,083 A | 12/1997 | Nelson, Jr. |
| 5,716,628 A | 2/1998 | Vinopal et al. |
| 5,854,266 A | 12/1998 | Nelson, Jr. |
| 5,886,031 A | 3/1999 | Shin et al. |
| 5,974,569 A | 10/1999 | Nickles |
| 6,017,562 A | 1/2000 | Kaufman et al. |
| 6,017,936 A | 1/2000 | Polson et al. |
| 6,162,446 A | 12/2000 | Hani et al. |
| 6,242,007 B1 | 6/2001 | Mohseni et al. |
| 6,277,360 B1 | 8/2001 | Carew et al. |
| 6,432,432 B1 | 8/2002 | Mohseni et al. |
| 6,451,300 B1 | 9/2002 | Dunlop et al. |
| 6,465,015 B1 | 10/2002 | Mohseni et al. |
| 6,500,792 B2 | 12/2002 | Riesgraf et al. |
| 6,649,155 B1 | 11/2003 | Dunlop et al. |
| 6,673,756 B2 | 1/2004 | Sonnenberg et al. |
| 6,682,724 B2 | 1/2004 | Mohseni et al. |
| 6,908,912 B2 | 6/2005 | Rioux et al. |
| 7,026,308 B1 | 4/2006 | Gavin et al. |
| 7,455,851 B1 | 11/2008 | Nelson et al. |
| 7,544,367 B2 | 6/2009 | Mohseni et al. |
| 7,674,785 B2 | 3/2010 | Gavin et al. |
| D646,979 S | 10/2011 | Shaw et al. |
| D656,839 S | 4/2012 | Shaw et al. |
| 8,206,732 B2 | 6/2012 | Nelson et al. |
| 8,324,455 B2 | 12/2012 | Puzio et al. |
| 2002/0001605 A1 | 1/2002 | Carew et al. |
| 2004/0058855 A1 | 3/2004 | Schwartz et al. |
| 2004/0213751 A1 | 10/2004 | Schwartz et al. |
| 2005/0027595 A1 | 2/2005 | Ha et al. |
| 2005/0118276 A1 | 6/2005 | Lei et al. |
| 2006/0111259 A1 | 5/2006 | Chakrabarty et al. |
| 2007/0009463 A1 | 1/2007 | Niebauer et al. |
| 2007/0009472 A1 | 1/2007 | Niebauer et al. |
| 2008/0249136 A1 | 10/2008 | Annis et al. |
| 2009/0214628 A1* | 8/2009 | De Rijk .................. 424/450 |
| 2012/0219610 A1 | 8/2012 | Smith, III et al. |
| 2013/0045961 A1 | 2/2013 | Smith, III et al. |
| 2013/0081155 A1 | 3/2013 | Puzio et al. |

FOREIGN PATENT DOCUMENTS

| | | |
|---|---|---|
| EP | 0158481 A2 | 10/1985 |
| EP | 0196824 A2 | 10/1986 |
| EP | 0217635 A2 | 4/1987 |
| EP | 0285388 A2 | 10/1988 |
| JP | 2001-278863 | 1/2001 |
| WO | 99/66886 A1 | 12/1999 |
| WO | 02/00178 A1 | 1/2002 |

* cited by examiner

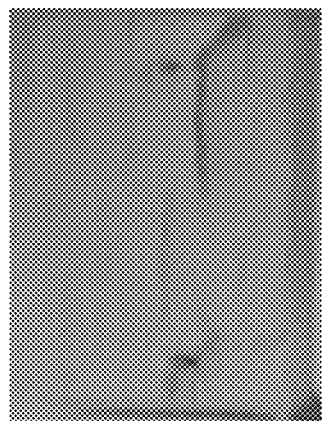
COMPARATIVE EXAMPLE 2
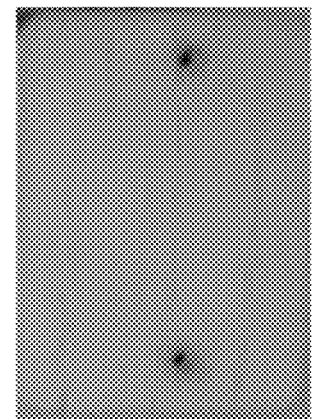
COMPARATIVE EXAMPLE 3
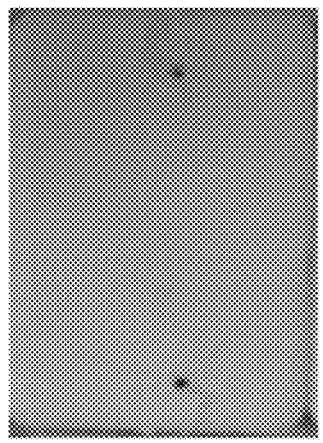
EXAMPLE 5
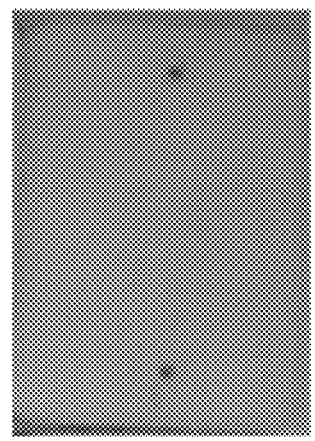
EXAMPLE 6
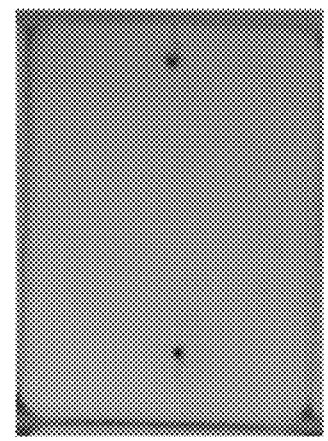
EXAMPLE 7

BAR SOAP COMPRISING PYRITHIONE SOURCES

CROSS REFERENCE TO RELATED APPLICATIONS

This application claims the benefit of PCT China Application No. PCT/CN2011/000320, filed Feb. 28, 2011.

FIELD OF THE INVENTION

The present invention relates to a bar soap comprising pyrithione sources.

BACKGROUND OF THE INVENTION

Pyrithione sources, such as sodium pyrithione or zinc pyrithione (hereinafter, ZPT) have been known widely used to provide an antimicrobial efficacy for a broad list of industrial applications. For example, sodium pyrithione and zinc pyrithione have been employed as preservatives against the growth of micro-organism in personal care compositions, paints, adhesives and so on. Another application of pyrithione source, for example, is the wide use of ZPT as an antidandruff agent in hair care products.

Bar soap is a popular product form for cleansing. A bar soap comprising pyrithione source for antimicrobial efficacy can be desired. However, during manufacturing, handling or storage of a bar soap, various metallic parts of the manufacturing equipment, for example pipes, nozzles may be contacted with the bar soap. In some situation, such contact can maintain a long time (e.g. overnight to 24 hours), and at a relatively elevated temperature.

Such contact has the potential of causing a color change of the bar soap, so called "discoloration", which is from a colored precipitate. The precipitate is a reaction resultant of pyrithione source with dissolved metal ions, such as ferric ions and/or cupric ions from the metal parts of the equipment. The discoloration can also be brought about by dissolved metal ions as metal contaminants in raw materials used for making bar soap, such as fatty esters.

In one aspect, this discoloration of a bar soap is unwanted for aesthetic reasons, where certain desirable colors are important to meet the consumer's needs. Consumer dissatisfaction and economic loss can result from such discoloration. In another aspect, the formation of a colored pyrithione precipitate is unwanted for a safety and regulatory consideration. For example, a green discoloration from copper pyrithione may stain stratum corneum, resulting a bar soap that is not suitable for body cleaning or facial cleaning.

In the past, a number of solutions toward this pyrithione discoloration problem have been described. For example, in U.S. Pat. No. 4,161,526, JP Patent Publication 2001-278863A, U.S. Pat. Nos. 4,482,715, 4,957,658 and 4,818,436, a number of materials including zinc-containing materials, borates, reducing agents selected from alkali metal sulfite, alkali metal bisulfites, hydrazine and mixtures thereof and HEDP have been used to address the pyrithione discoloration problem.

However, those solutions may be less desired for safety reason, for regional regulatory reasons, and/or for cost reasons and the like.

Specifically, the use of zinc-containing compounds may be less desired in solving this discoloration problem because: 1) soluble zinc level limitations from regional regulatory authorities, as there are countries like China that limit the maximum soluble zinc salt level excluding those zinc contributed by ZPT or zinc phenolsulfonate to be 1% in a cosmetic composition and 2) adoption of such zinc materials may not be very cost effective.

As to the use of reducing agents, they tend to interact with other ingredients in bar soap, thus posing challenges in formulation and process.

As to the use of HEDP, the amount of HEDP chelant incorporated in a bar soap needs to be very carefully controlled in order not to chelating some metal ions which is useful in bar soap formulation.

Hence, there still exists a need for a bar soap comprising a pyrithione source, which is free of discoloration problem, is cost effective and is free of the shortcomings of discoloration prevention approaches in the art mentioned above. The present invention provides such solutions.

SUMMARY OF THE INVENTION

The present invention relates to a bar soap comprising a pyrithione source, a soap surfactant, and a pH adjusting agent selected from a group consisting of ammonia solution, triethanolamine, diethanolamine, monoethanolamine, potassium hydroxide, sodium hydroxide, sodium phosphate dibasic, soluble carbonate salts and combinations thereof, wherein said soap attains a pH of greater than or equal to 10.7. This bar soap shows a decreased discoloration.

The present invention also relates to a process of inhibiting the formation of a discoloration in a bar soap caused by the reaction of ferric ion or cupric ion and pyrithione sources in the bar soap comprising the step of adding pH adjuster during manufacturing the bar soap to attain a pH of greater than or equal to 10.7, wherein the pH adjusting agent selected from a group consisting of ammonia solution, triethanolamine, diethanolamine, monoethanolamine, potassium hydroxide, sodium hydroxide, sodium phosphate dibasic, soluble carbonate salts and combinations thereof.

BRIEF DESCRIPTION OF THE DRAWINGS

FIG. 1 shows photos taken of the surfaces of 5 different bar soaps of Examples 5-7 and comparative Examples 2-3 pierced with iron nails, which are used to compare the discoloration inhibition efficacy between the present bar soap and comparative bar soap.

DETAILED DESCRIPTION OF THE INVENTION

The present invention relates to a bar soap comprising a pyrithione source, a soap surfactant, and a pH adjusting agent selected from a group consisting of ammonia solution, triethanolamine, diethanolamine, monoethanolamine, potassium hydroxide, sodium hydroxide, sodium phosphate dibasic, soluble carbonate salts and combinations thereof, wherein the soap attains a pH of greater than or equal to 10.7. This bar soap shows a decreased discoloration.

Without being bound by theory, it is believed that by increasing the pH, a configuration change of the pyrithione group happens, making the pyrithione group tend not to react with the dissolved ferric or cupric ions to form colored precipitates, thereby inhibiting or decreasing discoloration.

Specifically, pyrithione, i.e., 1-hydroxy-2-pyridinethione, is an aromatic heterocycle related to pyridine as shown in Formula 1.

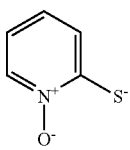

(1)

Via the sulfur and the oxygen of its N-hydroxythioamide group, it forms a complex (as shown in formula 2) with a transitional metal, which may be selected from the group consisting of zinc ion, ferric ion and cupric ion, but is not limited to these. The chemical structure of the N-hydroxythioamide group in the pyrithione anion species gives rise to a bidentate character due to the negative charge and the adjacent strong electron donor potential, and it is this allowing the coordination with metal cations such as zinc, copper or ion.

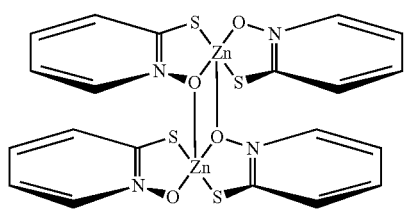

(2)

According to Irving & Williams Series, the smaller an ionic radius is, the more stable of the coordination between pyrithione and the metal ion. $Fe^{3+}$ has a radius of 0.64A which is smaller than that of $Cu^{2+}$ 0.73A, and which in turn is smaller than that of $Zn^{2+}$ 0.74A. This helps explain the formation of undesired pyrithione discoloration in the existence of other pyrithione source, such as zinc pyrithione.

However, due to tautomerism and acid-base equilibria, pyrithione is subject to speciation, as shown in equilibrium scheme (I).

Equilibrium Scheme (I)

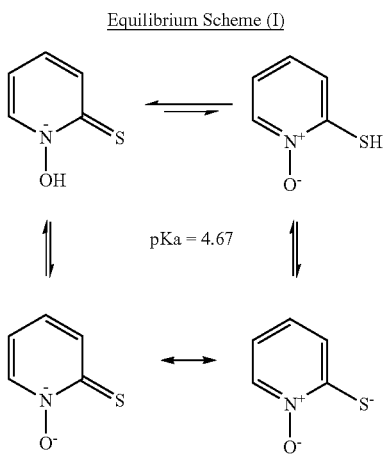 [SMILES: On1ccccc1=S ; [O-][n+]1ccccc1S ; [O-]n1ccccc1=S ; [O-][n+]1ccccc1[S-]]

It is believed by the present inventor that an increased pH plays a role in turning the equilibrium of the pyrithione speciation from the pyrithione carrying a positively charged nitrogen atom (shown in the equilibrium scheme II below on the right) to a negatively charged nitrogen atom(shown in the left of the equilibrium scheme II is incapable of coordinating with metal ion including ferric ion. Free ferric ions can then turn into $Fe(OH)_3$ and finally $Fe_2O_3$ under increased pH condition, and further prevent the formation of undesired colored ferric pyrithione.

Equilibrium Scheme (II)

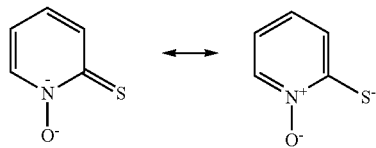

Discoloration

As used herein, "discoloration" means the color change brought by colored precipitates formed from a reaction of pyrithione source with unwanted dissolved metal ions, such as ferric ions and/or cupric ions. The discoloration can be in a color of grayish blue, blue, black, purple, green and the other colors, which are different from an original color of a bar soap comprising a pyrithione source. By "original color", it means the color of the bar soap before the pyrithione source in the bar reacts with ferric and/or cupric ion.

A number of ways are available for measuring discoloration. Details of measurement are described in later section of the present specification under DISCOLORATION MEASUREMENT.

Pyrithione Source

As used herein, the pyrithione source can be a pyrithione and a pyrithione salt capable of providing antimicrobial efficacy. Preferred pyrithione salts are those formed from heavy metals such as zinc, tin, cadmium, magnesium, aluminum and zirconium. Zinc salts are most preferred, especially the zinc salt of 1-hydroxy-2-pyridinethione (zinc pyridinethione, also named zinc pyrithione, ZPT). Other cations such as sodium may also be suitable. The pyrithione source may be selected from the group consisting of sodium pyrithione, zinc pyrithione, magnesium disulfide pyrithione, pyrithione acid, dipyrithione, chitosan pyrithione and combinations thereof. Preferably, it is sodium pyrithione or zinc pyrithione and more preferably, it is a zinc pyrithione (ZPT). ZPT is commercially available from various suppliers. For example, ZPT FPS available from Arch Chemical can be used. It is an aqueous dispersion comprising 48% active ZPT. Pyrithione sources are well known in the personal cleansing art, and are described, for example, in U.S. Pat. Nos. 2,809,971; 3,236,733; 3,753,196; 3,761,418; 4,345,080; 4,323,683; 4, 379, 753; and 4,470,982. Descriptions about pyrithione sources in the above mentioned patents are incorporated herein by reference.

The pyrithione source can be present in the present composition in an amount ranging from about 0.05%, 0.1% or 0.4% to about 0.5%, 2% or 5%.

Soap Surfactant

The bar soap of the present invention will typically comprise a soap surfactant, or in short "soap", in an amount ranging from about 40%, 45%, 50% to about 65%, 75%, 84%. The term "soap" is used herein in its popular sense, i.e., the alkali metal or alkanol ammonium salts of alkane- or alkene monocarboxylic acids. Sodium, magnesium, potassium, calcium, mono-, di- and tri-ethanol ammonium cations, or combinations thereof are suitable for purposes of the present invention. In general, sodium soaps are used in the compositions of this invention, but from about 1% to about 25% of the soap may be ammonium, potassium, magnesium, calcium or a mixture of these soaps. The soaps useful herein are the well known alkali metal salts of alkanoic or alkenoic acids having about 12 to 22 carbon atoms, preferably about 12 to about 18 carbon atoms. They may also be described as alkali metal carboxylates of alkyl or alkene hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It can be preferred to use soaps having the fatty acid distribution of tallow and vegetable oil. More preferably, the vegetable oil is selected from the group consisting of palm oil, coconut oil, palm kernel oil, palm oil stearine, and hydrogenated rice bran oil, or mixtures thereof, since these are among the more readily available fats. Especially preferred are palm oil stearine, palm kernel oil, and/or coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principal chain lengths are C16 and higher.

A preferred soap is sodium soap having a mixture of about 50% tallow, 30% palm oil stearine, and 20% palm kernel oil or coconut oil. The soaps may contain unsaturated fatty acid in accordance with commercially acceptable standards. An excessive degree of unsaturation in the soap is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

PH and PH Adjusting Agents

The pH of the present bar soap is greater than or equal to 10.7, preferably greater than or equal to 11, 11.5, 12, 12.5, 13, and 13.5, till up to 14. As used herein, pH of the present composition is measured at around 25° C. using any commercially available pH meter. When the tested composition is in a solid form, it is first dissolved in distilled water to form an aqueous solution of a concentration of 10%. The pH of this aqueous solution is then tested to be representative of the bar soap.

The present bar soap comprises a pH adjusting agent in a sufficient amount to attain the above mentioned pH. The pH adjusting agents useful for the present composition includes alkalizing agents. Suitable alkalizing agents include, for example, ammonia solution, triethanolamine, diethanolamine, monoethanolamine, potassium hydroxide, sodium hydroxide, sodium phosphate dibasic, soluble carbonate salts, ammonia solution, triethanolamine, diethanolamine, monoethanolamine, potassium hydroxide, sodium hydroxide, sodium phosphate dibasic, soluble carbonate salts and combinations thereof.

The amount of the pH adjusting agent required to attain the requisite pH can be calculated by one skilled in the art following known chemical parameters, for example, pKa value of the pH adjusting agent.

In one embodiment of the present invention, the present bar soap comprises a soluble carbonate salt presented in an amount effective to attain a pH of greater than or equal to 10.7 to decrease discoloration. Soluble carbonate salts may include those carbonates and bicarbonates that have a solubility of greater than or equal to 0.01 g in water at 20° C. Such carbonates can be selected from a group consisting of sodium carbonate, potassium carbonate, ammonium carbonate, aluminum carbonate, magnesium carbonate, sodium bicarbonate, potassium bicarbonate, ammonium bicarbonate and combinations thereof.

The present composition comprises a soluble carbonate salt in an amount effective to prevent discoloration. For example, soluble carbonate salt is present in the present composition in an amount ranging from about 0.3%, 0.5%, 0.8%, 1% or 1.5% to about 2%, 2.5%, 5%, 10% or 20%.

Zinc Source

The present composition may additionally comprise a zinc source. Suitable zinc source include those zinc-containing materials described in U.S. Pat. No. 4,161,526, which can also provide discoloration inhibiting benefit. Specifically, the zinc source is selected from a group consisting of a zinc salt of an organic carboxylic zinc salt, inorganic zinc salt, zinc hydroxide, zinc oxide, and combinations thereof. In one embodiment, the zinc source is zinc carbonate and/or zinc oxide.

The zinc source, for example; zinc carbonate is also known as being able to potentiate the efficacy of the pyrithione source. The present composition comprises from 0.01% to 0.5% of a zinc source.

In one embodiment of the present invention, the present bar soap comprises 0.5% zinc pyrithione, 2% sodium carbonate, and 0.1% zinc carbonate.

Other Ingredients

The bar soap can additionally comprise inorganic salts. Inorganic salts can help to bind the water in the bar composition thereby reducing water activity ("Aw") of water in the present compositions and preventing water loss by evaporation or other means.

Structurants can also optionally be included as ingredients in the present bar soap. Suitable structurants in the present compositions include raw starch (e.g. corn, rice, potato, wheat, and the like), pregelatinzed starch, carboxymethyl cellulose, polyacrylate polymer available under the trade name of Stabylene from BF Goodrich and Carbopol from 3V Corporation, carregeenan, xanthan gum, polyethylene glycol, polyethylene oxide, and the like. Preferred structurants include raw starch and/or pregelatinized starch.

Free fatty acid can optionally be added to the present bar soap compositions to provide enhanced skin feel benefits such as softer and smoother feeling skin. Suitable free fatty acids include those derived from tallow, coconut, palm and palm kernel.

Synthetic surfactants can be optionally utilized in the present bar compositions to further improve the lathering properties of the bar soap during use. The synthetic surfactants useful in this invention include anionic, amphoteric, nonionic, zwitterionic, and cationic surfactants.

Brighteners can be included as optional ingredients in the present compositions at a level of from about 0.001% to about 1%, preferably from about 0.005% to about 0.5%, and more preferably from about 0.01% to about 0.1%, by weight of the composition.

Silica, or silicon dioxide, can be optionally incorporated in the present bar compositions at a level of from about 0.1% to about 15%, preferably from about 1% to about 10%, and more preferably from about 3% to about 7%, by weight of the composition. Silica is available in a variety of different forms include crystalline, amorphous, fumed, precipitated, gel, and colloidal. Preferred forms herein are fumed and/or precipitated silica.

Other optional ingredients in the present bar compositions include: perfumes, sequestering agents, coloring agents, opacifiers and pearlizers such as titanium dioxide. All of these are useful in enhancing the appearance or cosmetic properties of the product.

The appearance of the bar composition according to the present invention can be transparent, translucent, or opaque. In one embodiment, the bar composition is opaque.

Preparation Method

Bar soaps are customarily prepared either by framing/casting or by milling/plodding. Framed or cast soaps are typically prepared by reacting an appropriate fat, oil or carboxylic acid with a base in the presence of water to form soap, pouring the molten soap into a frame or a mold, allowing the soap to cool and harden. Milled/plodded soap bars are produced by subjecting the neutralized soap to various finishing steps which alter the crystalline matrix of the soap from the omega phase, as formed in framed/cast soap bars, to the beta phase.

The present bar soap can be made using any of the above mentioned manufacturing processes, and the pyrithione source and pH adjusting agent can be added during the mixing steps of preparing the bar soaps.

Measurement Method

PH Measurement

As used herein, pH of the present bar soap is measured at around 25° C. using any commercially available pH meter. The bar soap is first dissolved in distilled water at 35° C. and agitated for a hour, to form an aqueous solution of a concentration of 10%. The solution is cooled down to 25° C. and the pH is measured.

Discoloration Measurement

One method of quantitatively measuring discoloration inhibition efficacy is described. First, the soap is dissolved in water to reach a 10% solution following the process described above for soap solution preparation for pH measurement. Then the ferrate is added into the soap solution to reach a total iron concentration of 20 ppm based on the weight of the solution. Then the color (L value) of the soap solution before and after adding ferrate is measured to get a delta L by deducting the value measured before adding from the value after adding. Here, "L" stands for brightness or whiteness of the sample measured. The absolute value of delta L divided by the original L value measured before adding ferrate is expressed as a percentage. When the percentage is less than 7%, preferably less than 5%, 3%, 1%, 0.5%, the sample bar can be considered as having decreased discoloration problem. A spectrophotometer (e.g., Macbeth COLOR-EYE 3100 spectrophotometer from Gretagmacbeth) can be used to measure the L value.

Another method of showing the discoloration inhibition efficacy is an iron nail piercing test. This test mimics the real life situation where the bar soap comprising a pyrithione source has a chance of contacting metallic surfaces during manufacturing and/or during consumer use in a high moisture environment, thereby causing a discoloration problem. In the piercing test, a bar soap which has been pierced with and now containing an embedded iron source, is soaked completely under water for 30 minutes at room temperature. Then, the water is removed and let the bar stand for 24 hours at room temperature. Then, the iron nails are removed then and the bar soap surface is checked for discoloration at the area where the iron nail contacts the bar.

EXAMPLES

In order to test the effectiveness of increasing pH in reducing blue discoloration caused by dissolved ferric ion in a bar soap comprising pyrithione source, the following experiments are conducted. Present examples 1-7 illustrated the bar soap compositions of the present disclosure, but are not intended to be limiting thereof.

Examples 1-4 and Comparative Example 1

The bar soaps of Examples 1-4 and Comparative Example 1 comprising the ingredients listed below in Table 1.

TABLE 1

| | Comparative Example 1 | Ex. 1 | Ex. 2 | Ex. 3 | Ex. 4 |
|---|---|---|---|---|---|
| Soap noodles | 97.5 | 93.7 | 81.1 | 97.25 | 97.0 |
| Titanium dioxide | 0.5 | 0.5 | 0.5 | 0.5 | 0.5 |
| Perfume | 0.5 | 0.5 | 0.5 | 0.5 | 0.5 |
| brightener | 0.04 | 0.04 | 0.04 | 0.04 | 0.04 |
| ZPT* | 1.0 | 1.0 | 1.0 | 1.0 | 1.0 |
| Sodium carbonate | — | 3.8 | 16.4 | — | — |
| Sodium hydroxide | — | — | — | 0.25 | 0.50 |
| Water | Balance | Balance | Balance | Balance | Balance |
| pH (10% sol) | 9.96 | 10.79 | 11.05 | 10.92 | 11.74 |
| ΔL | 17.4% | 6.9% | 0.6% | 7.0% | 0.8% |

The soap noodles are made via a conventional process involving a crutching step and a vacuum drying step. The soap noodles are then added to an amalgamator. The ingredients of water, titanium dioxide, brightener and perfume are then added to the amalgamator and mixed for about 30 to 60 seconds. This soap mixture is then processed through conventional milling, plodding, and stamping steps to yield the finished bar soap compositions. The soap noodle utilized in these examples 1-4 and comparative example 1 have the following approximate composition: about 50% sodium palmate, 16% sodium tallowate, 14.5% sodium palm kernelate, about 3% glycerin, about 0.5% sodium chloride, and about 15% water, the balance being unsaponifiables. These percentage amounts are by weight of the soap noodle. ZPT used here, is available from Arch Chemical under the name of ZPT FPS, which is a 48% aqueous dispersion.

The bar soap having this composition is dissolved in water at a temperature of 35° C. and agitated for 1 hour to reach a 10% aqueous solution. $FeCl_3$ solution is then added into the 10% aqueous soap solution to reach a final concentration of measured total irons at 20 ppm by weight of the aqueous solution (or 200 ppm by weight of the bar soap).

The L value measured before addition of ferric ion is set as the blank control for calculating $\Delta L$ value. The final row in the above Tables 1 shows the measurement representing the difference in the "L" value (whiteness value) between the blank control and the corresponding sample comprising $Na_2CO_3$ or NaOH and dissolved ferric ion.

The results given in Table 1 above show that the addition of sodium carbonate in Examples 1-2 and the addition of sodium hydroxide in Examples 3-4, which both adjust the pH of the bar soap solution to be greater than 10.7, has significantly reduced the discoloration caused by the ferric ion with zinc pyrithione. The $\Delta L$ changes in Examples 1-4 are all less than 7%. Comparative Example 1 which has pH of 9.96 and does not comprise pH adjusting agent to reach pH of 10.7, shows a much higher $\Delta L$ value of 17.4%.

Examples 5-7 and Comparative Examples 2-3

The bar soaps of Examples 5-7 and Comparative Examples 2-3 comprising the ingredients listed below in Table 2 are made following essentially the same manufacturing method as previously described for Examples 1-4 and Comparative Example 1. Zinc oxide and zinc carbonate in the present Examples 6 and 7 are mixed with soap noodles, together with titanium dioxide et. al. The soap noodles here are the same as those used in Examples 1-4 and Comparative Example 1.

TABLE 2

| | Comparative Example 2 | Comparative Example 3 | Ex. 5 | Ex. 6 | Ex. 7 |
|---|---|---|---|---|---|
| Soap noodles | 98.5 | 98.1 | 96.1 | 96.05 | 96.05 |
| Titanium dioxide | 0.5 | 0.5 | 0.5 | 0.5 | 0.5 |
| Perfume | 0.5 | 0.5 | 0.5 | 0.5 | 0.5 |
| brightener | 0.04 | 0.04 | 0.04 | 0.04 | 0.04 |
| ZPT* | — | 0.4 | 0.4 | 0.4 | 0.4 |
| Sodium carbonate | — | — | 2 | 2 | 2 |
| Zinc oxide | — | — | — | 0.05 | — |
| Zinc carbonate | — | — | — | — | 0.05 |
| Water | Balance | Balance | Balance | Balance | Balance |
| pH (10% sol) | | <10.7 | | >10.7 | |

The finished bar soaps are pierced with an iron nail following the protocol described previously in the DISCOLORATION MEASUREMENT section for discoloration inspection.

The iron nail used here is made of carbon steel and has a diameter of 1.5 mm and a length of 15 mm. The iron nail is pierced into the bar at a depth of around 10 mm. The iron nail is pretreated with sand paper to remove rust before being pierced into bar soap.

FIG. 1 shows the photo taken of the surfaces of 5 different exemplary bar soaps. It can be seen that Comparative Example 2 bar soap comprising no ZPT does not show discoloration on the nail pierced surface, while Comparative Example 3 comprising 0.4% ZPT shows dark blue discoloration around the pierced area, and each of the bar soaps of Examples 5-7 shows no discoloration when they comprises sodium carbonate to achieve a pH of greater than 10.7.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A bar soap comprising a pyrithione source, a soap surfactant, and a pH adjusting agent selected from a group consisting of ammonia solution, triethanolamine, diethanolamine, monoethanolamine, potassium hydroxide, sodium hydroxide, soluble carbonate salts, and combinations thereof, wherein said soap attains a pH of greater than or equal to 10.7.

2. The bar soap of claim 1, wherein said pyrithione source is selected from a group consisting of zinc pyrithione, sodium pyrithione, pyrithione acid, dipyrithione, chitonsan pyrithione, magnesium disulfide pyrithione, and combinations thereof.

3. The bar soap of claim 1, wherein said soluble carbonate salt is selected from a group consisting of sodium carbonate, potassium carbonate, ammonium carbonate, aluminum carbonate, magnesium carbonate, sodium bicarbonate, potassium bicarbonate, and combinations thereof.

4. The bar soap of claim 3, wherein said soluble carbonate is present in an amount of from about 0.3% to about 20%.

5. The bar soap of any one of previous claims, further comprising a zinc source selected from the group consisting of an organic carboxylic zinc salt, an inorganic zinc salt, zinc hydroxide, zinc oxide, and combinations thereof, wherein the zinc source is in present in an amount of from about 0.01% to about 0.5%.

6. The bar soap of claim 5, wherein said zinc source is zinc carbonate and/or zinc oxide.

7. The bar soap of claim 1, comprising as a pyrithione source 0.5% zinc pyrithione, as a pH adjusting agent 2% sodium carbonate, and further comprising as a zinc source 0.1% zinc carbonate.

8. A process of inhibiting the formation of a discoloration in a bar soap caused by the reaction of dissolved ferric ions and/or cupric ions with pyrithione sources in the bar, comprising the step of adding a pH adjusting agent during manufacturing of the bar soap to attain a pH of greater than or equal to 10.7, wherein said pH adjusting agent is selected from a group consisting of ammonia solution, triethanolamine, diethanolamine, monoethanolamine, potassium hydroxide, sodium hydroxide, soluble carbonate salts, and combinations thereof.

9. A process of inhibiting the formation of a discoloration in a bar soap caused by the reaction of dissolved ferric ions and/or cupric ions with pyrithione sources in the bar, comprising the step of adding from about 0.3% to about 20% of soluble carbonate salt during manufacturing of the bar soap.

* * * * *